United States Patent [19]

Ledin-Bonevik

[11] Patent Number: 4,696,673
[45] Date of Patent: Sep. 29, 1987

[54] COLON IRRIGATOR FOR USE WITHIN A TOILET BASIN

[76] Inventor: Birgitta B. M. Ledin-Bonevik, Vintervägen 9, S-542 00 Mariestad, Sweden

[21] Appl. No.: 821,735
[22] PCT Filed: Mar. 29, 1985
[86] PCT No.: PCT/SE85/00146
§ 371 Date: Nov. 27, 1985
§ 102(e) Date: Nov. 27, 1985
[87] PCT Pub. No.: WO85/04331
PCT Pub. Date: Oct. 10, 1985

[30] Foreign Application Priority Data

Mar. 30, 1984 [SE] Sweden ............................. 8401786

[51] Int. Cl.⁴ ............................................. A61M 37/00
[52] U.S. Cl. ................................ 604/150; 4/420.1; 4/420.4; 4/448
[58] Field of Search ..................... 604/149-154; 4/420.1-420.4, 231, 443, 445, 447, 448

[56] References Cited

U.S. PATENT DOCUMENTS

| | | | |
|---|---|---|---|
| 1,025,189 | 5/1912 | Jackson | 4/231 |
| 1,838,356 | 12/1931 | Berry | 4/420.1 |
| 2,826,761 | 3/1958 | Lazarus et al. | 4/447 |
| 3,288,140 | 11/1966 | McCarthy | 4/420.1 |
| 3,430,268 | 3/1969 | Zoberg | 4/447 |
| 4,383,339 | 5/1983 | Miller | 4/448 |

FOREIGN PATENT DOCUMENTS 2106014 2/1971 Fed. Rep. of Germany.

Primary Examiner—C. Fred Rosenbaum
Attorney, Agent, or Firm—Sughrue, Mion, Zinn, Macpeak & Seas

[57] ABSTRACT

A device intended to be attached to a toilet basin to permit irrigation of the colon, comprises a tube (2) which is carried by a holder (1) and having end connected to a water container located at a higher level than the toilet stool and the other end connected to a rectum catheter via a check valve. The holder (1) is provided with two sprung attachment arms (7) which project from the (1) in two mutually opposite directions and in a common plane. The arms are arranged, when the holder is inserted into the cavity of a toilet basin, to fix the holder (1) in a given position at the rear part of the basin as a result of the sprung abutment of the arms (7) against the basin walls, so that the rectum catheter extends substantially vertically upwards. The attachment arms suitably comprise arcuate wire rods (7) or bands, which abut the basin walls immediately beneath the flush water outlets.

7 Claims, 2 Drawing Figures

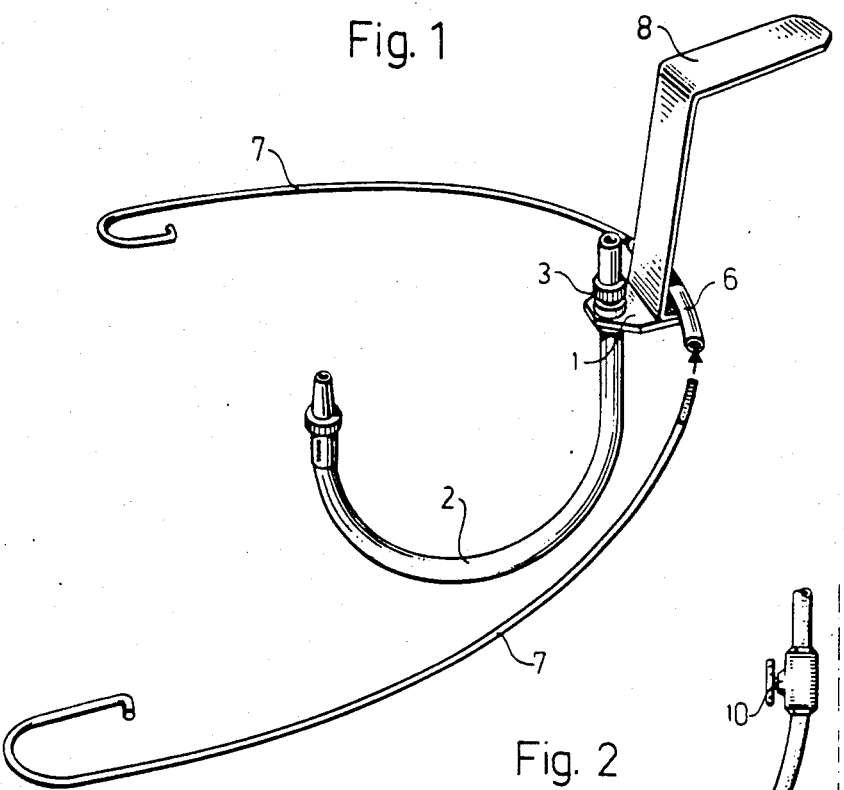
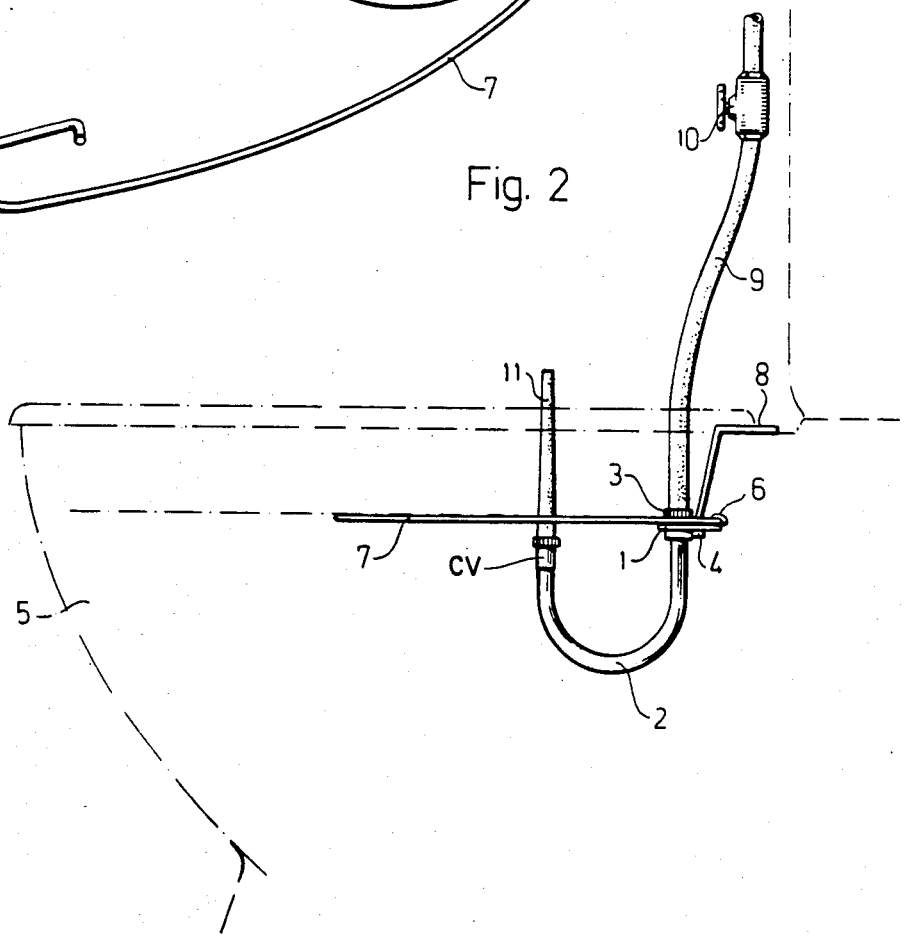

COLON IRRIGATOR FOR USE WITHIN A TOILET BASIN

BACKGROUND OF THE INVENTION

The present invention relates to a device intended for attachment to a toilet basin to permit rinsing of the colon with liquid (enema). The device comprises a tube which is carried by a holder and one end of which is intended for connection to a water tank located at a higher level than the toilet basin or to another water supply, and the other end of which is intended for connection, suitably via a check valve, to a rectum catheter (enema catheter), the holder being arranged to be fixed in a given position in the cavity of a toilet basin with the rectum catheter extending substantially vertically upwards with the use of spring attachment arms intended for co-action with the toilet basin.

In hospitals and like nursing establishments an enema or colon irrigation is normally given with the patient lying on a bed or some suitable horizontal surface. The patient is then moved to a toilet, where the water introduced into the bowel is allowed to run out therefrom. Because the patient has to be moved from the bed to the toilet, the procedure often becomes unsanitary and causes discomfort both to the patient and to the nursing personnel. The fact that water is introduced into the bowel with the patient in a recumbent position may also cause discomfort to the patient, due to too large a quantity of water being administered. It is also difficult for a person to administer an enema in this way by himself-/herself, without assistance.

In the Swedish lay-open print No. 315 553 there is described a colon irrigator which can be used while seated on a toilet seat. To this end the device includes an auxiliary seat which is to be placed on the toilet basin and which has mounted thereon a supply tube for rinsing or treatment liquid, and a rectum catheter. This device has the advantage of rendering it unnecessary to move the patient. In addition, the bowel is filled with water with the patient in a sitting position, which affords certain advantages. This known device also enables the patient himself/herself to effect an enema without assistance.

The known device is encumbered with a number of disadvantages, among which are included the following. The additional loose seat which must be placed on the toilet basin is considered unsafe or unstable, especially by older and infirm people, since the auxiliary seat is prone to slide sideways. This renders it difficult for the patient to relax properly. In addition, the device as a whole, including seat and tube connection, is very bulky, which among other things prevents it from being taken readily as baggage when people who require regular irrigation of the colon travel. In order to sterilize the device in an autoclave it is necessary to dismantle the device from the toilet basin, which requires a number of working operations to be carried out and renders the task relatively complicated. Furthermore, the known device cannot be made universally compatible to all toilet designs.

SUMMARY OF THE INVENTION

The main object of the invention is to provide a device of the aforesaid kind which while providing the same advantages as the device known from the aforesaid Swedish lay-open print is not encumbered, inter alia, with the aforesaid disadvantages, and which is therefore both easier and safer to use, and also easy to store, transport and sterilize.

In accordance with the present invention a device of the aforementioned kind is particularly characterized in that the spring attachment arms extend in mutually opposite directions on the holder in a common horizontal plane and are arranged, when in use, to resiliently abut mutually opposite wall portions of the toilet basin, with one arm on either side of the centre line of the toilet basin.

When using a device according to the invention the patient thus sits comfortably in a normal fashion on the seat belonging to the toilet basin, since the whole of the device is located at a lower position within the basin. The patient is therefore able to sit firmly on the seat and be perfectly relaxed.

The attachment arms preferably have the form of arcuate wires or bands arranged to abut the basin walls immediately beneath the flush outlet lip. The arms will therefore lie in a relatively protected position and will not block the toilet.

The attachment arms are suitably constructed to enable them to be readily removed from the holder, which, in the in-use position, may have the form of a near flat plate provided with holes in which the aforesaid tubular piece can be detachably secured. Among other things, this enables the device to be readily dismantled for sterilization in an autoclave, and also enables it to be packed into a very small package for transport purposes.

In order to prevent the rectum catheter from being displaced laterally, the plate and the aforesaid tube are preferably provided with co-acting means which enable the tube to be held firmly in a given position of rotation relative to the plate. The holder is also suitably provided with means which co-act with the upper edge of the toilet basin to prevent the holder from sliding down thereinto.

BRIEF DESCRIPTION OF THE DRAWINGS

The invention will now be described in more detail with reference to an illustrative embodiment thereof shown in the accompanying drawing in which;

FIG. 1 is a perspective view of a device according to the invention; and

FIG. 2 is a side view of the device when mounted to a toilet basin.

DETAILED DESCRIPTION OF THE PREFERRED EMBODIMENTS

As will be seen from the drawing, the device includes a holder in the form of a plate 1 having a hole in which there is secured a U-shaped tube 2 with the aid of a nut 3. As shown in FIG. 2, the tube 2 is provided at a location on the underside of the plate with a shoulder 4 which, when fastening the tube, co-acts with a recess arranged in the plate in a manner to fixate the tube 2 in a given position of rotation relative to the plate 1.

It is intended that the plate 1 with the tube 2 can be attached to and removed from the basin of a toilet 5, shown in chain lines in FIG. 2, in a ready and simple fashion, to which end the plate 1 of the illustrated embodiment is connected with a horizontally arranged tubular holder 6. A spring attachment arm 7 is arranged for insertion into each of the ends of the holder 6. The arms 7 are identical and are located in a common horizontal plane and, when the device is inserted into the toilet basin or bowl, are intended to fix the plate with the tube 2 to the rear part of the toilet basin by resilient abutment of the arms with the basin walls.

The device can thus be readily mounted onto the toilet basin and provides very positive fixation of the holder, among other things because the basin has a downwardly narrowing form. Because the arms 7 are sprung and thus adaptable to different forms, the device can be attached to practically all makes of toilet basins. The arms 7 are therewith normally located so as to be protected beneath the flush water openings and do not block the toilet in any way. In order to eliminate any risk of the holder from sliding down into the toilet basin, the holder is provided with an angled handle 8, which lies against the upper edge surface of the toilet basin when the device is in use.

As shown in FIG. 2, one end of the tube 2 is connected to a hose 9 which, in turn, is connected via a tap 10 to a water container or tank located at a higher level than the toilet basin. The water container may, for example, be hung on a wall behind the toilet basin. The other end of the tube 2 is connected, via a check valve CV, with a rectum catheter 11, which as a result of the shape of the tube 2 extends substantially vertically upwards.

The device illustrated in FIG. 2 can be used by a person for colon irrigation without requiring the assistance of another person. The person is thus able to sit positively and firmly on the normal seat of the toilet basin, and irrigation can be effected with the person in a sitting position, without needing to move.

All components are suitably manufactured from a material resistant to corrosion, such as stainless steel, which enables the components to be sterilized in an autoclave. The device can herefore be readily and quickly dismantled and requires a minimum of space for packaging or storage purposes. As beforementioned, this enables the device to be taken on journeys without difficulty. Another important advantage afforded by the device is that it is compatible with to all types of toilet basins.

The invention is not restricted to the illustrated embodiment and many modifications can be made. This applies, for example, to the precise form of the holder and the spring arms respectively. For example, the arms may have the form of bands or the like, instead of wire or rod, wherewith each arm may also comprise a plurality of mutually parallel branches. For the purpose of readily inserting the device into the cavity of a toilet basin and removing the device therefrom, however, it is important that the arms are sprung, so that the device can be held firmly in position with the aid of the spring force thus provided.

What is claimed is:

1. A colon irrigation apparatus, comprising: a toilet basis (5) having a flushing outlet lip extending around an upper, inner periphery of a cavity of the basin, a colon irrigation device adapted to be readily attached to and removed from within said toilet basin and including a rigid rube (2) mounted to a rigid holder (1), one end of said tube being adapted for connection to a water container located at a higher level than the toilet basin (5) or to another water supply, and another, opposite end of said tube being connected to a rectum catheter (11) via a check valve (CV), the holder being disposed within the cavity of the toilet basin at the rear thereof with the rectum catheter extending substantially vertically upwardly in and above a central portion of the basin, and a pair of spring attachment arm means (7) extending laterally in mutually opposite directions from the holder in a common horizontal plane and arranged, when in use, to resiliently abut and engage mutually opposite inner wall portions of the toilet basin just under said flushing outlet lip thereof, with one arm on either side of the center line of the basin, said spring arm means being arcuate and generally conforming to the curvature of the inner wall of the basin, and being self-biased outwardly away from the center of the basin to ensure a firm engagement therewith.

2. An apparatus according to claim 1, wherein the attachment arm means are wire rods or bands.

3. An apparatus according to claim 1 or claim 2, wherein the attachment arm means are detachable from the holder.

4. An apparatus according to claim 1, wherein the holder is a substantially horizontal plate provided with a hole for the detachable mounting of said tube (2).

5. An apparatus according to claim 4, wherein the plate and said tube are provided with co-acting means (4) for holding the tube firmly in a given position of rotation relative to the plate.

6. An apparatus according to claim 1, wherein the holder is provided with means (8) for co-acting with the upper edge of the toilet basin to prevent the holder from sliding down thereinto.

7. An apparatus according to claim 1, wherein all components of the device are made of a stainless material capable of being sterilized in an autoclave.

* * * * *